United States Patent [19]

Cauwenbergh et al.

[11] Patent Number: 5,612,347
[45] Date of Patent: Mar. 18, 1997

[54] AGENTS FOR PRESERVING OR RESTORING THE SOUNDNESS OF THE SKIN

[75] Inventors: Gerard F. M. J. Cauwenbergh, Vorselaar; Marc J. De Brabander, Zoersel, both of Belgium

[73] Assignee: Janssen Pharmaceutica N.V., Beerse, Belgium

[21] Appl. No.: 342,666

[22] Filed: Nov. 21, 1994

Related U.S. Application Data

[63] Continuation of Ser. No. 705,684, May 24, 1991, abandoned, which is a continuation of Ser. No. 324,262, Mar. 15, 1989, abandoned, which is a continuation-in-part of Ser. No. 173,858, Mar. 28, 1988, abandoned.

[51] Int. Cl.$^6$ ............................................. A61K 31/505
[52] U.S. Cl. ..................... 514/259; 514/253; 514/258; 514/321; 514/323
[58] Field of Search ............................................. 514/256

[56] References Cited

U.S. PATENT DOCUMENTS 4,874,766  10/1989  Ooms et al. .......................... 514/258

OTHER PUBLICATIONS

Roget's International Thesaurus, 3rd edition, 1962, published by Thomas Y. Crowell Co., 690.13, p. 458.
H. Helmig, Wound Healing and Serotonin Antagonism An Experimental Animal Study, Praxis 58, (11), 337–342 (1969).
Chem. Abs. 103 No. 134811w (1985), Hechtman.
Chem. Abs. 105 No. 72377n (1986), Lagerkvist et al.
Chem. Abs. 109 No. 86874s (1988), De Ridder.
Biological Abs. 79 No. 24745 (1985), Roald et al.
Chem. Abs. 98 No. 100917w (1983), Stranden et al.
Chem. Abs. 102 No. 125264v (1985), Awouters et al.

*Primary Examiner*—Shelley A. Dodson
*Attorney, Agent, or Firm*—Charles J. Metz

[57] ABSTRACT

Agents for preserving or restoring the soundness of the skin by administering a serotonin antagonist which in particular is a compound of formula

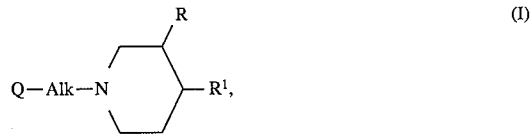

a salt or a stereoisomeric forms thereof; wherein Q is

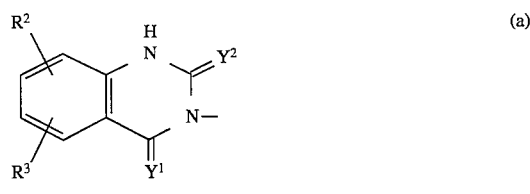

or

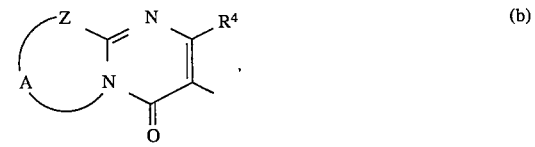

and R$^1$ is —X—Ar (c),

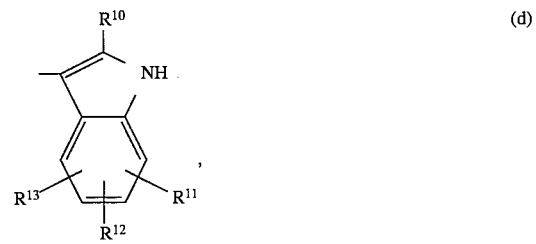

or

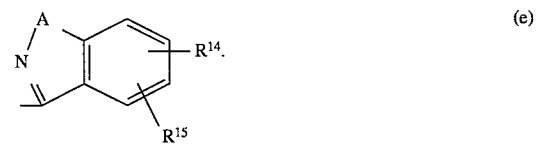

the agent of formula (I) preferably being ketanserin.

8 Claims, No Drawings

AGENTS FOR PRESERVING OR RESTORING THE SOUNDNESS OF THE SKIN

CROSS-REFERENCE TO RELATED APPLICATIONS

This application is a continuation of application Ser. No. 07/705,684, filed May 24, 1991, now abandoned, which was a continuation of application Ser. No. 07/324,262, filed Mar. 15, 1989, now abandoned, which in turn was a continuation-in-part of application Ser. No. 07/173,858, filed Mar. 28, 1988, now abandoned.

BACKGROUND OF THE INVENTION

The soundness of the skin can be disturbed by phenomena such as wrinkles, striae and keloids. Although such phenomena in general do not impose serious medical problems, they are often appreciated as inconveniences with more or less serious social implications.

Quite unexpectedly, it now has been found that compounds possessing serotonin antagonistic activity can be used in the preservation and restoration of the skin.

DESCRIPTION OF THE INVENTION

The present invention is concerned with a method of preserving or restoring the soundness of the skin in subjects in need of such preservation or restoration, said method comprising the administration to said subjects of an amount effective in preserving or restoring the said soundness, of a compound possessing serotonin-antagonistic activity, said compound in particular having the formula

$$Q\text{—Alk—N}\diagdown\diagup\text{—}R^1, \quad (I)$$

the pharmaceutically acceptable acid-addition salts thereof and the possible stereoisomeric forms thereof; wherein R is hydrogen or $C_{1-6}$alkyl;

Alk is $C_{1-4}$alkanediyl;

Q is a radical of formula

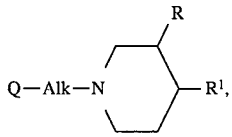

(a)

wherein $Y^1$ and $Y^2$ are each independently O or S;

$R^2$ is hydrogen, halo, $C_{1-6}$alkyl or $C_{1-6}$alkyloxy;

$R^3$ is hydrogen or halo; or

Q is a radical of formula

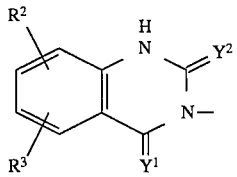

(b)

wherein $R^4$ is hydrogen or $C_{1-6}$alkyl;

Z is —S—, —CH$_2$— or —CR$^5$=CR$^6$—; said $R^5$ and $R^6$ each independently being hydrogen or $C_{1-6}$alkyl; and A is a bivalent radical —CH$_2$—CH$_2$—, —CH$_2$—CH$_2$—CH$_2$— or —CR$^7$=CR$^8$—, said $R^7$ and $R^8$ each independently being hydrogen, halo, amino or $C_{1-6}$alkyl;

$R^1$ is a radical of formula

—X—Ar   (c)

wherein Ar is phenyl or substituted phenyl, said substituted phenyl bearing an amino group and/or 1, 2 or 3 halo atoms; and

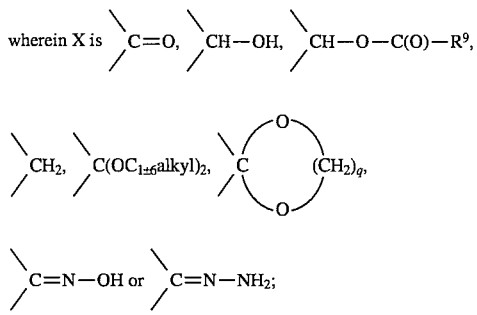

said $R^9$ being hydrogen or $C_{1-6}$ alkyl and said q being the integer 2 or 3; or $R^1$ is a radical of formula

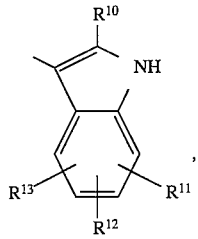

(d)

wherein $R^{10}$ is hydrogen or $C_{1-6}$alkyl; $R^{11}$, $R^{12}$ and $R^{13}$ are each independently hydrogen or halo;

or $R^1$ is a radical of formula

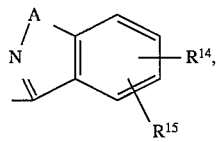

(e)

wherein A is O or S; $R^{14}$ and $R^{15}$ are each independently hydrogen, halo, hydroxy, $C_{1-6}$alkyloxy or $C_{1-6}$alkyl.

As used in the foregoing definitions the term halo is generic to fluoro, chloro, bromo and iodo; the term "$C_{1-6}$alkyl" defines straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; and "$C_{1-4}$alkanediyl" is meant to include bivalent straight or branch chained alkanediyl radicals having from 1 to 4 carbon atoms.

Preferred compounds of formula (I) according to the present invention are those wherein $R^1$ is a radical of formula (c).

Particularly preferred compounds of formula (I) according to the present invention are those preferred compounds of formula (I) wherein Q is a radical of formula (a) wherein $Y^1$ and $Y^2$ are both oxygen atoms and $R^2$ and $R^3$ are both hydrogen; or wherein Q is a radical of formula (b), wherein $R^4$ is methyl, Z is —$CR^5$=$CR^6$— wherein $R^5$ and $R^6$ are independently hydrogen or methyl, A is —$CR^7$=$CR^8$— wherein $R^7$ and $R^8$ are independently hydrogen or methyl; and/or wherein in the radical (c) X is C=O and Ar is halo substituted phenyl.

The most preferred compounds according to the present invention are selected from the group consisting of 3-[2-[4-(4-fluorobenzoyl)-1-piperidinyl]ethyl]-2,4-(1H, 3H-quinazolinedione which compound is generically designated as ketanserin, and 3-[2-[4-(4-fluorobenzoyl)-1-piperidinyl]ethyl]-2,7-dimethyl-4H-pyrido-[1,2-a]-pyrimidin-4-one and the pharmaceutically acceptable acid-addition salts thereof.

The compounds of formula (I) can be used as such or in their acid-addition salt form. The latter can conveniently be obtained by treating the base-form with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) preferably used in the method of the present invention are known serotonin antagonists and their preparation as well as their pharmacological properties have been described in U.S. Pat. Nos. 4,335,127, 4,342,870, 4,443,451, 4,665,075, and 4,804,663, all incorporated herein by reference.

The serotonin-antagonistic compounds used in the method of the present invention are most preferably applied in the form of appropriate compositions, in particular compositions usually employed for the topical administration of drugs or cosmetic compositions. Said compositions contain the active ingredient and a skin-acceptable carrier. They may take a wide variety of forms such as, for example, solid forms, e.g. powders; liquid forms, e.g. solutions or suspensions in aqueous or oily mediums; semi-liquid formulations, e.g. creams, gellies, pastes, ointments, salves.

Other such compositions are preparations of the cosmetic type, such as toilet waters, packs, lotions, skin milks or milky lotions. Thus, the said preparations may contain, besides the active ingredient, components usually employed in such preparations, examples of such components being oils, fats, waxes, surfactants, humectants, thickening agents, antioxidants, viscosity stabilizers, chelating agents, buffers, preservatives, perfumes, dyestuffs, lower alkanols. If desired, further ingredients may be incorporated in the compositions, e.g. anti-inflammatory agents, antibacterials, antifungals, disinfectants, vitamins, sunscreens, anti-acne agents, antibiotics, etc. . .

Examples of oils comprise fats and oils such as olive oil, and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxyethylene polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate and citric acid ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient will be incorporated in the said compositions, said active ingredient preferably being ketanserin. In ointments or creams, the carrier for example consists of 1 to 20%, in particular 5 to 15% of a humectant, 0.1 to 10% in particular from 0.5 to 5% of a thickener and water, or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, any % refers to a % by weight. The humectant, surfactant, oil, etc. . . . referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the active ingredients of formula (I) are formulated in liposome containing compositions. Liposomes are products formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when phospholipids or other suitable amphiphathic molecules are allowed to swell in water or aqueous solutions to form liquid crystals usually of multilayer structure comprised of many bilayers separated from each other by aqueous material. Another type of liposome is known consisting of a single bilayer encapsulating aqueous material which may also be referred to as a unilamellar vesicle. If water-soluble materials are included in the aqueous phase during the swelling of the lipids they become entrapped between the lipid bilayers.

Water-soluble active ingredients such as, for example, most of the salt forms of the compounds of formula (I) are encapsulated in the aqueous spaces between the molecular layers. Lipid soluble active ingredients, e.g. most of the base forms of the compounds of formula (I), are incorporated into the lipid layers, although polar head groups may protrude from the layer into the aqueous space. The encapsulation of these compounds can be achieved by a number of methods. The method most commonly used involves casting a thin film of phospholipid onto the walls of a flask by evaporation of an organic solvent. When this film is dispersed in a suitable aqueous medium, multilamellar liposomes are formed (also referred to as coarse liposomes). Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysation or some other suitable procedure. Lipid-soluble active ingredients are usually incorporated by dissolving them in the organic solvent with the phospholipid prior to casting the film. If the solubility of these materials in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of the active ingredients of formula (I) is the method described in EP-A-253,619, incorporated herein by reference. In this method, single bilayered liposomes containing encapsulated active ingredients are prepared by dissolving the lipid component being the predecessor of the liposomes in an organic medium, injecting under pressure the organic solution of the lipid component into an aqueous component while simultaneously mixing the organic and aqueous components with a high speed homogenizer or mixing means, whereupon the liposomes are formed spontaneously.

The single bilayered liposomes containing encapsulated active ingredient of formula (I) can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatidylethanolamine, phosphatydylserine, phosphatidylinositol, lysophosphatidylcholine and phosphatidyl glycerol, for example. Other lipophilic additives may be employed in order to selectively modify the characteristics of the liposomes. Examples of such other additives include stearylamine, phosphatidic acid, tocopherol, cholesterol and lanolin extracts.

It may be advantageous to use micronized forms of the active ingredient, i.e., material having an average particle size of less than 10 microns, as the high surface area will facilitate the dissolution of the liposomal components.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such as benzoic acid, methyl paraben and propyl paraben may also be added.

The liposome-formulated forms of the active ingredients of the present invention, particularly those obtained in the above-referred method of preparing such liposome formulated forms, may be used as such or in combination with any of the aforementioned carriers to prepare ointments, creams, jellies, toilet waters, etc. . . .

Apart from the above-described compositions, use may be made of covers, e.g. plasters, bandages, dressings, gauze pads and the like, containing an appropriate amount of a composition as referred hereinabove. In some cases use may be made of plasters, bandages, dressings, gauze pads and the like which have been impregnated or sprinkled with a liquid formulation containing the active agent, e.g. with an aseptic aqueous solution, or strewn with a powdery solid composition, or smeared, covered or coated with a semi-liquid composition.

The active ingredient of formula (I) may also be applicated by iontophoresis or by local injection, e.g. syringe or dermojet. In the latter modes of application the compositions conveniently will be in a liquid form. For applications based on iontophoresis use will be made of liquid formulations containing acid addition salts of the active ingredients of formula (I).

The term skin used hereinabove, also referred to as cutis, is meant to comprise the outer integument or covering of the body, consisting of the dermis and epidermis. As disturbances of the skin soundness there may be mentioned all kinds of skin striae, such as, striae atrophicae, striae albicantes, associated with pregnancy (striae gravidarum) obesity, obesity followed by slimming, emaciation, rapid growth, e.g. during puberty or adolescence. Further disturbances comprise wrinkles, in particular fine wrinkling e.g. at an early stage of skin aging. Such disturbances may be caused by excessive stretching of the skin (stretch-marks), aging, exposure to wind, water, in particular sea water, sunlight. As other disturbances of the skin soundness there may be mentioned keloids and scars, in particular small scars. Examples of the latter are acne caused scars (for example acne induced pitting), hypertrophic scars and the like.

In a further aspect of the present invention, there is provided a composition containing as active ingredient a serotonin antagonist which preferably is a compound of formula (I) as defined hereinabove, and a carrier, and, if desired one or more further active ingredients. In general, the said composition may contain from 0.01% to 10% of the active ingredient, and in particular from 0.1% to 5%. Said compositions can be prepared following methods generally employed in the art of pharmaceutical formulation, e.g., for preparing powders by thoroughly grinding and mixing the components; for solutions by dissolving the active ingredient in the liquid medium by shaking, stirring, if desirable, at higher temperatures; for semi-liquid formulations by dispersing the active ingredient in the semi-liquid carrier, and the like methods. The following examples are intended to illustrate the scope of the present invention in all its aspects, and not to limit it thereto.

EXAMPLES

A. Composition examples

As used in the following examples Pluronic L35® is a trademark for a block-copolymer containing polyoxyethylene and polyoxypropylene blocks.

Example 1

3-[2-[4-(4-fluorobenzoyl)- 1-piperidinyl]ethyl]-2,4( 1H,3H-quinazolinedione (ketanserin) 0.25%:

| | |
|---|---|
| 3-[2-[4-(4-fluorobenzoyl)-1-piperidinyl]ethyl]-2,4(1H,3H)-quinazolinedione tartrate | 3.46 mg |
| propylene glycol | 99.0 mg |
| hydroxypropylmethylcellulose | 15.6 mg |
| water | 881.9 mg |

The active ingredient ketanserin tartrate is added to the water under vigorous stirring, whereupon the other ingredients are added.

Example 2

3-[2-[4-(4-fluorobenzoyl)-1-piperidinyl]ethyl]-2,7-dimethyl-4H-pyrido-[1,2-a]-pyrimidin-4-one 0.25%:

| | |
|---|---|
| 3-[2-[4-(4-fluorobenzoyl)-1-piperidinyl]ethyl]-2,7-dimethyl-4H-pyrido[1,2-a]pyrimidin-4-one | 2.5 mg |
| propyleneglycol | 99.0 mg |
| hydroxypropylmethylcellulose | 15.6 mg |
| water | 881.9 mg |

Example 3

| | |
|---|---|
| Ketanserin microfine | 2% |
| Pluronic L 35* | 90.5% |
| Glycerol monostearate | 7.5% |

Method of Preparation

Glycerol monostearate and Pluronic L 35* are introduced into a doublewall jacketed vessel and are heated to approximately 65° C. Stirring is applied until a homogeneous, clear liquid is obtained. This clear liquid is cooled to approximately 40° C., while gently stirring. Hereupon a slightly viscous, unctuous mass is formed. Subsequently, while homogenizing the mixture, ketanserin is sucked into the ointment by evacuating the vessel. Homogenizing is applied until ketanserin is evenly distributed in the ointment. The ointment is further cooled to 20°–25° C. while gently stirring.

Example 4

| | |
|---|---|
| Ketanserin microfine | 2% |
| Polyethyleneglycol 400 | 78% |
| Polyethyleneglycol 4000 | 20% |

Method of Preparation

Polyethyleneglycol 4000 and polyethyleneglycol 400 are introduced into a doublewall jacketed vessel and are heated to approximately 65° C. Stirring is applied until a homogeneous, clear liquid is obtained. This clear liquid is cooled to approximately 40° C., while gently stirring. Hereupon a slightly viscous, unctuous mass is formed. Subsequently, while homogenizing the mixture, ketanserin powder is sucked into the ointment by evacuating the vessel. Homogenizing is applied until ketanserin is evenly distributed in the ointment. The ointment is further cooled to 20°–25° C., while gently stirring.

Example 5

| | |
|---|---|
| Ketanserin | 5 g |
| Tartaric acid | 3 g |
| Anhydrous dextrose | 50 g |
| Propylene glycol | 51.8 g |
| water (ad 1 l) | 914.2 g |

Method of Preparation

In 500 ml of hot (90°–95° C.) sterile water are dissolved 50 ml of propylene glycol, 3 g of tartaric acid and 5 g of ketanserin, while stirring. A solution of 50 g of anhydrous dextrose in 250 ml of water is added to the former solution. The whole is diluted with sterile water to 1 l yielding a liquid preparation for dermojet or iontophoresis applications.

Example 6

As referred to in the following example Lipoid S45® is a trade mark for a formulation containing 49.0% of phosphatidyl choline, 48.0% of non-polar lipoids, 0.1% of DL-α-Tocopherol (vitamin E) and water.

| | |
|---|---|
| Ketanserin tartrate | 3.5 mg |
| Lipoid S45 (liquid) ® | 100.0 mg |
| Cholesterol | 10.0 mg |
| methylparaben | 2.0 mg |
| propylparaben | 0.02 mg |
| methyl cellulose | 15.0 mg |
| Distilled water ad | 1000.0 mg |
| Methanol p.a. | 400.0 µl |
| Chloroform p.a. | 800.0 µl |

Procedure 1

3.5 mg of ketanserin tartrate 100.0 mg of Lipoid S54® and 10.0 mg of cholesterol are dissolved while stirring in a mixture of 0.4 ml methanol and 0.8 ml of chlorophorm. Subsequently the latter solvents are evaporated in vacuo (temperature 40°–50° C.) (solution 1).

0.02 mg of propylparaben and 2.0 mg of methylparaben are dissolved in distilled water of a temperature of 80°–90° C. (solution 2). The latter solution 2 is cooled and added to solution 1 through a tube while homogenizing with a suitable high-performance homogenizer (solution 3).

15 mg of methylcellulose are humidified with 3 ml of distilled water of a temperature of 80°–90° C. The latter is added to solution 3 while intensively stirring upon homogenization.

Procedure 2

100 mg of Lipoid S45® and 10 mg of cholesterol are warmed while stirring till a clear solution is obtained (solution 1 ). 2 mg methylparaben and 0.02 mg of propylparaben are dissolved in distilled water having a temperature of 80°–90° C. This solution is allowed to cool and subsequently added through a tube to solution 1 while homogenizing with a high-performance homogenizer (solution 2). 15 mg of methylcellulose are humidified with 3 ml of distilled water having a temperature of 80°–90° C. The latter is added to solution 2 while vigourously stirring upon homogenization.
B. Clinical Examples The useful skin soundness preserving and/or restoring properties of the serotonin-antagonistic compounds to be used in the method of the present invention can be demonstrated by the following experiments.

Example 7

Six patients with stretchmarks (striae induced by pregnancy or physical exercise) were treated with daily applications of 2% ketanserin ointment (formulation of example 3). The stretchmarks had been present for periods ranging from 4 weeks to more than one year. After a minimum application time of one month, all 6 patients reported a significant decrease in the visibility and appearance of the striae.

Four patients with keloids which had been present for periods of 2 years up to more than 10 years were treated with ketanserin applications by dermojet or by iontophoresis. The formulation used in the latter applications was the formulation of example 5. Three patients had a keloid with presternal localization and one had a keloid on his back. Ketansefin has been applied during 3 weeks to 3 months. The 2 patients with the shortest treatment showed moderate improvement of their keloids (reduced size and hardness). Two patient have continued the treatment for 3 months. In one of them the keloid had disappeared completely. The second patient had experienced a marked reduction of the keloid.

Six patients with hypertrophyc scars present for 1 month up to 1 year received topical ketansefin in an ointment, by dermojet or by iontophoresis. Treatment lasted for 2 to 3.5 months. All patients experienced improvement or complete disappearance of their scars. Another patient had acne induced pitting in his face. This had been present for 1 year. Daily applications of 2% topical ketansefin for 2.5 months virtually restored the normal skin morphology. None of these 17 patients reported side effects.

What is claimed is:

1. A method for treating a skin condition selected from the group consisting of skin striae, wrinkles, keloids and scars after formation, and acne induced pitting in subjects in need of such treatment, said method comprising the administration to the skin of said subjects of an amount effective to treat said condition of a serotonin antagonist comprising a compound of the formula:

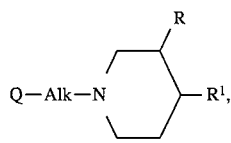

a pharmaceutically acceptable acid-addition salt thereof and the possible stereoisomeric form thereof; wherein:

R represents hydrogen or $C_{1-6}$alkyl;

Alk represents $C_{1-4}$alkanediyl;

Q represents a radical of the formula:

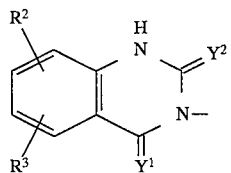

wherein $Y^1$ and $Y^2$ each independently represent O or S; $R^2$ represents hydrogen, halo, $C_{1-6}$alkyl or $C_{1-6}$alkyloxy; and $R^3$ represents hydrogen or halo; or Q represents a radical of the formula:

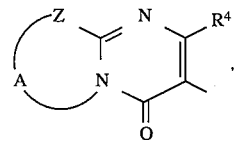

wherein $R^4$ represents hydrogen or $C_{1-6}$alkyl; Z represents —S—, —$CH_2$—, or —$CR^5$=$CR^6$—, wherein said $R^5$ and $R^6$ each independently represent hydrogen or $C_{1-6}$alkyl; and A represents a bivalent radical —$CH_2$—$CH_2$—, —$CH_2$—$CH_2$—$CH_2$— or —$CR^7$=$CR^8$— wherein said $R^7$ and $R^8$ each independently represent hydrogen, halo, amino, or $C_{1-6}$alkyl; and $R^1$ represents a radical of the formula:

wherein Ar represents phenyl or substituted phenyl, said substituted phenyl bearing an amino group, 1, 2, or 3 halo atoms, or both an amino group and 1, 2, or 3 halo atoms; and X represents —CO—, —CH(OH)—, —CH(O—CO—$R^9$)—, —$CH_2$—, —C[(O$C_{1-6}$alkyl)$_2$]—, —C(=N—OH)—, —C(=N—$NH_2$)—, or

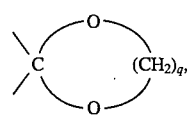

wherein $R^9$ represents hydrogen or $C_{1-6}$alkyl and q represents 2 or 3; or 5,612,347

11

R¹ represents a radical of the formula:

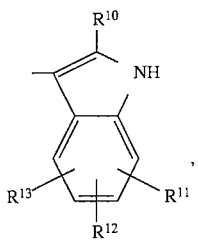
(d)

wherein R¹⁰ represents hydrogen or $C_{1-6}$alkyl; and R¹¹, R¹², and R¹³ each independently represent hydrogen or halo;

or R¹ represents a radical of the formula:

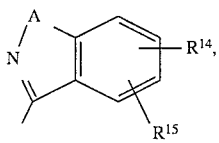
(e)

wherein A represents O or S; and R¹⁴ and R¹⁵ each independently represent hydrogen, halo, hydroxy, $C_{1-6}$alkyloxy, or $C_{1-6}$alkyl.

2. A method according to claim 1 wherein the compound of formula (I) is ketanserin.

3. A method for treating a skin condition selected from the group consisting of skin striae, wrinkles, keloids and scars after formation, and acne induced pitting in subjects in need of such treatment, which method comprises the administration to the skin of said subjects of a cosmetic composition, which composition comprises a cosmetic carrier and as active ingredient a compound of the formula:

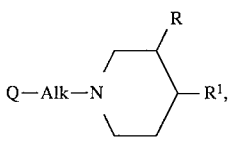
(I)

a pharmaceutically acceptable acid-addition salt thereof and the possible stereoisomeric form thereof; wherein:

R represents hydrogen or $C_{1-6}$alkyl;

Alk represents $C_{1-4}$alkanediyl;

Q represents a radical of the formula:

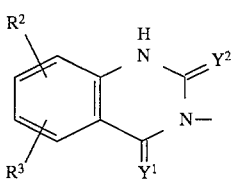
(a)

wherein Y¹ and Y² each independently represent O or S; R² represents hydrogen, halo, $C_{1-6}$alkyl or $C_{1-6}$alkyloxy; and R³ represents hydrogen or halo; or Q represents a radical of the formula:

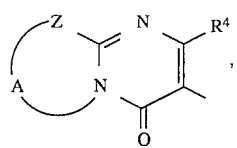
(b)

wherein R⁴ represents hydrogen or $C_{1-6}$alkyl; Z represents —S—, —CH₂—, or —CR⁵=CR⁶—, wherein said R⁵ and R⁶ each independently represent hydrogen or $C_{1-6}$alkyl; and A represents a bivalent radical —CH₂—CH₂—, —CH₂—

12

CH₂—CH₂— or —CR⁷=CR⁸—, wherein said R⁷ and R⁸ each independently represent hydrogen, halo, amino, or $C_{1-6}$alkyl; and R¹ represents a radical of the formula:

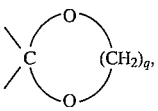
(c)

wherein Ar represents phenyl or substituted phenyl, said substituted phenyl bearing an amino group, 1, 2, or 3 halo atoms, or both an amino group and 1, 2, or 3 halo atoms; and X represents —CO—, —CH(OH)—, —CH(O—CO—R⁹)—, —CH₂—, —C[(OC$_{1-6}$alkyl)₂]—, —C(=N—OH)—, —C(=N—NH₂)—, or

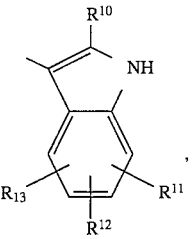

wherein R⁹ represents hydrogen or $C_{1-6}$alkyl and q represents 2 or 3; or

R¹ represents a radical of the formula:

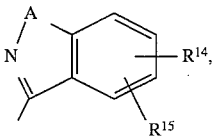
(d)

wherein R¹⁰ represents hydrogen or $C_{1-6}$alkyl; and R¹¹, R¹², and R¹³ each independently represent hydrogen or halo;

or R¹ represents a radical of the formula:

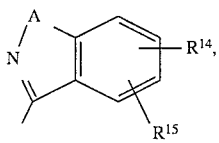
(e)

wherein A represents O or S; and R¹⁴ and R¹⁵ each independently represent hydrogen, halo, hydroxy, $C_{1-6}$alkyloxy, or $C_{1-6}$alkyl.

4. A method according to claim 3 wherein the active ingredient is ketanserin or a pharmaceutically acceptable acid addition salt thereof.

5. A method according to claim 3 wherein the composition is a cream, an ointment, a toilet water or a skin milk.

6. A method for treating a skin condition selected from the group consisting of skin striae, wrinkles, keloids and scars after formation, and acne induced pitting in subjects in need of such treatment, which method comprises the administration to the skin of said subjects of a cosmetic composition, which composition comprises a cosmetic carrier and as active ingredient a compound of the formula:

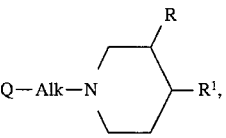
(I)

a pharmaceutically acceptable acid-addition salt thereof and the possible stereoisomeric form thereof; wherein:

R represents hydrogen or $C_{1-6}$alkyl;

Alk represents $C_{1-4}$alkanediyl;

Q represents a radical of the formula:

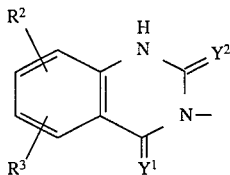   (a)

wherein $Y^1$ and $Y^2$ each independently represent O or S; $R^2$ represents hydrogen, halo, $C_{1-6}$alkyl or $C_{1-6}$alkyloxy; and $R^3$ represents hydrogen or halo; or Q represents a radical of the formula:

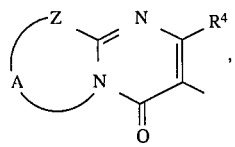   (b)

wherein $R^4$ represents hydrogen or $C_{1-6}$alkyl; Z represents —S—, —$CH_2$—, or —$CR^5=CR^6$—, wherein said $R^5$ and $R^6$ each independently represent hydrogen or $C_{1-6}$alkyl; and A represents a bivalent radical —$CH_2$—$CH_2$—, —$CH_2$—$CH_2$—$CH_2$— or —$CR^7=CR^8$—, wherein said $R^7$ and $R^8$ each independently represent hydrogen, halo, amino, or $C_{1-6}$alkyl; and $R^1$ represents a radical of the formula:

   (c)

wherein Ar represents phenyl or substituted phenyl, said substituted phenyl bearing an amino group, 1, 2, or 3 halo atoms, or both an amino group and 1, 2, or 3 halo atoms; and X represents CO—, —CH(OH), —CH(O—CO—$R^9$)—, —$CH_2$—, —C[(O$C_{1-6}$alkyl)$_2$]—, —C(=N—OH)—, —C(=N—$NH_2$)—, or

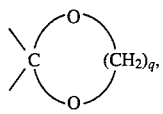

wherein $R^9$ represents hydrogen or $C_{1-6}$alkyl and p represents 2 or 3; or $R^1$ represents a radical of the formula:

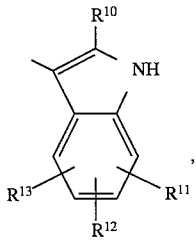   (d)

wherein $R^{10}$ represents hydrogen or $C_{1-6}$alkyl; and $R^{11}$, $R^{12}$, and $R^{13}$ each independently represent hydrogen or halo;

or $R^1$ represents a radical of the formula:

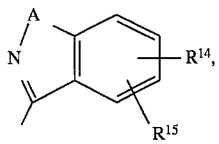   (e)

wherein A represents O or S; and $R^{14}$ and $R^{15}$ each independently represent hydrogen, halo, hydroxy, $C_{1-6}$alkyloxy, or $C_{1-6}$alkyl, wherein said compound is encapsulated in a liposome and an inert carrier.

7. A method according to claim 6 wherein the compound of formula (I) is ketanserin.

8. A method according to claim 7 wherein the liposome is a single bilayered liposome.

* * * * *